United States Patent [19]

Seidel et al.

[11] 4,298,441

[45] Nov. 3, 1981

[54] METHOD OF PRESERVING THE ELECTROPHORETIC PROPERTIES OF LIPOPROTEINS

[75] Inventors: Dietrich Seidel, Heidelberg; Heinrich Wieland, Waake, both of Fed. Rep. of Germany; Ewald Molinari, Mödling, Austria

[73] Assignee: Immuno Aktiengesellschaft für chemisch-medizinische Produkte, Vienna, Austria

[21] Appl. No.: 159,672

[22] Filed: Jun. 16, 1980

[30] Foreign Application Priority Data

Jun. 27, 1979 [AT] Austria .................................. 4484/79

[51] Int. Cl.³ .......................................... G01N 27/26
[52] U.S. Cl. ........................... 204/180 G; 204/180 S; 204/299 R; 23/230 B; 424/12; 252/408
[58] Field of Search .......... 204/180 G, 180 S, 180 R, 204/299 R; 424/12; 23/230 B; 252/408; 250/303; 195/68

[56] References Cited

U.S. PATENT DOCUMENTS

| | | | |
|---|---|---|---|
| 3,836,433 | 9/1974 | Wirth et al. | 195/68 |
| 3,873,433 | 3/1975 | Seidel et al. | 204/299 X |
| 4,001,583 | 1/1977 | Barrett | 250/303 |
| 4,046,723 | 9/1977 | Dorman | 424/12 X |
| 4,127,502 | 11/1978 | Mutti et al. | 23/230 B X |
| 4,147,606 | 4/1979 | Golias | 204/180 G X |

*Primary Examiner*—Arthur C. Prescott
*Attorney, Agent, or Firm*—Brumbaugh, Graves, Donohue & Raymond

[57] ABSTRACT

A method of preserving the electrophoretic properties of lipoproteins in human or animal plasma, plasma fractions or sera, in which the lipoprotein pattern is to be electrophoretically determined, consists in that non-reducing sugars are added to the plasma, plasma fractions or sera, the mixture is lyophilized and the lyophilizate is reconstituted prior to determination.

6 Claims, 3 Drawing Figures

METHOD OF PRESERVING THE ELECTROPHORETIC PROPERTIES OF LIPOPROTEINS

The invention relates to a method of preserving the electrophoretic properties of lipoproteins, in particular of LDL, VLDL and HDL lipoproteins, in human or animal plasma, plasma fractions or sera, in which the lipoprotein pattern is to be determined electrophoretically.

A method of demonstrating lipoprotein patterns in human or animal body liquids is described in U.S. Pat. No. 3,873,433. The method consists in that the lipoproteins contained in the body liquids are electrophoretically separated in a carrier medium, such as a gel, or on foils, wherein, after the desired separation effect has occurred, the carrier is treated with a developing solution comprising one or more of the following substances: polyanions, such as heparin or dextran sulfate, sodium dodecylsulfate, sodium phosphotungstate, sodium oleate, sodium salts of bile acids, suitably in the presence of bivalent cations, such as magnesium and calcium, as well as NaCl if desired, wherein complex salts of low solubility are formed with the lipoproteins. The complex salts of the individual lipoproteins form bands on the carrier medium, which bands can be quantitatively evaluated by densitometry, a precise picture of the quantitative distribution of the various lipoproteins in the serum being obtained.

Determinations of this kind are particularly necessary for the diagnosis of different forms of hyperlipoproteinemia. The described method of determining the lipoprotein patterns, however, requires a considerable time consumption so that it is frequently not possible, in particular with mass examinations, to carry out the determination immediately or shortly after the taking of blood. However, when storing the lipoproteins for few days only, the native composition of the lipoproteins will irreversibly change, which holds particularly for the unstable lipoproteins LDL, VLDL and HDL.

Previous efforts to ensure the stability and storing capacity over a longer period of time of the samples to be examined, have had no satisfactory success so far. Thus, it has for instance proved that lyophilization does not suffice. Also in lyophilized samples, the unstable lipoproteins will irreversibly change already during a short storing period.

The desire to maintain and to preserve the native composition of the lipoproteins, is appropriate in particular also for the quality assurance of control sera, for which legal stipulations have been established in most countries of the world. So far, it has not been possible to preserve the qualitative and quantitative electrophoretic properties of lipoproteins in human or animal body liquids in a control serum, and therefore it has not been possible to make sure of the analysis of lipoprotein spectri with control sera. There has thus been the demand for a control serum which can be analyzed as to its natural lipoprotein content and which can be maintained in a stable form over a longer period of time.

The invention aims at avoiding the difficulties described and has as its object to preserve the intact molecule structure of the lipoproteins in plasma, plasma fractions or sera, until they have been electrophoretically separated and are determinable in their native form. A further aim of the invention is to provide control sera containing lipoproteins, to ensure their quality and thus to provide the possibility of controlling electrophoretic lipoprotein analyses.

These objects are achieved according to the invention in that non-reducing sugars, in particular sucrose, are added to the plasma or plasma fractions, respectively, or to the sera, the mixture is lyophilized and the lyophilizate is reconstituted before determination.

Advantageously, the non-reducing sugars are added in an amount of 10 to 20% w/v.

A further preferred embodiment of the invention consists in that the sugar-containing mixture is shock-frozen at at least $-70°$ C. prior to lyophilization, whereupon the mixture is lyophilized after heating to $-40°$ C. to $-35°$ C.

It is true that U.S. Pat. No. 4,127,502 has already indicated that a serum matrix or serum-derived composition containing lipids can be stabilized by the addition of sugar, sugar amines or sugar alcohols, and subsequent lyophilization, the reconstituted mixture showing a decrease in the optical density. Yet, this earlier proposal does not deal with the preservation of the electrophoretic properties of lipoproteins. The lipids mentioned in the earlier proposal have another composition than the lipoproteins. They contain no protein components, in particular no apoprotein portions. However, it is the latter which are responsible for the rapid decomposition of native lipoprotein molecules.

In addition to the possibility of storing lipoprotein-containing examination samples over longer periods of time and providing a reliable control serum for lipoprotein diagnostics, the method according to the invention also allows for an unfalsified analytic procedure of all the remaining components present in the plasma, i.e. of the electrolytes sodium, potassium, calcium, of creatine, urea, anorganic phosphate, iron, of the lipids cholesterin, triglycerides and phospholipids, and of uric acid; furthermore, the enzymatic activities in the plasma can be measured, such as GOT, GPT, CPK, alkaline phosphatase, acid phosphatase, gamma GT, amylase. Moreover, also a determination of glucose, bilirubin, total protein as well as of certain protein fractions, such as albumin, globulin and further subfractions, is feasible without problems.

It has proved that sera that have been stabilized according to the invention, in particular control sera, remain stable and unchanged during storage for at least one year, even when stored at $37°$ C.

The invention will now be explained in more detail by way of the accompanying drawing, wherein.

Figure 1:
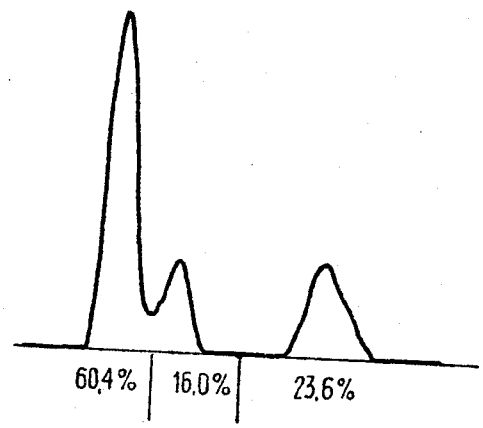
FIG. 1 shows an electropherogram of a freshly taken native serum.

In the evaluation according to FIG. 1, the contents of $\beta$-lipoprotein, pre-$\beta$-lipoprotein and $\alpha$-lipoprotein have been recorded by the recorder of a densitometer in native form immediately after the blood was taken. The first peak identifies the relative percents of $\beta$-lipoprotein as 60.4%, the second peak identifies those of pre-$\beta$-lipoprotein as 16.0% and the third peak identifies those of $\alpha$-lipoprotein as 23.6%.

Figure 2:
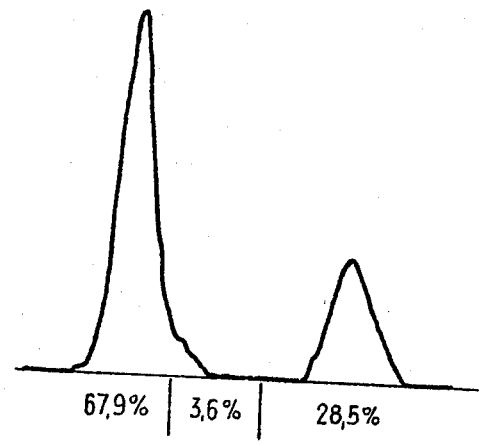
FIG. 2 is an electropherogram of the same serum frozen and lyophilized immediately after taking and stored for one week before determination.

From FIG. 2 it can be seen that the ratio of $\beta$-lipoprotein to pre-$\beta$-lipoprotein changed after a one-week storage. The pre-$\beta$-lipoprotein peak has vanished almost entirely. The integrator evaluation incorrectly indicates 67.9% of β-lipoprotein, 3.6% of pre-β-lipoprotein and 28.5% of α-lipoprotein.

Figure 3:
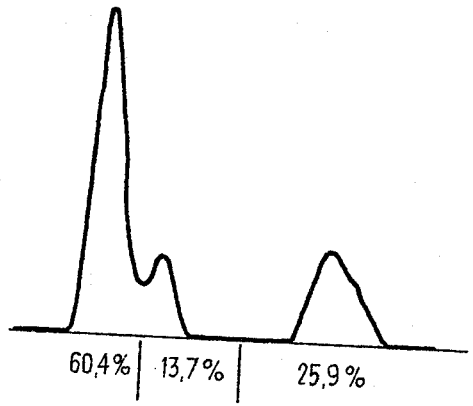
FIG. 3 shows an electropherogram of a serum according to the invention preserved by the addition of 12% w/v of sucrose and stored for one year.

In the electropherogram of FIG. 3, however, which was obtained after a treatment according to the invention, the pre-β-lipoprotein peak remained the same, and the integrator evaluation showed 60.4% of β-lipoprotein, 13.7% of pre-β-lipoprotein and 25.9% of α-lipoprotein—which comes very close to the original composition.

What we claim is:

1. A method of preserving the electrophoretic properties of lipoproteins, in particular of LDL, VLDL and HDL lipoproteins, in human or animal plasma, plasma fractions or sera, in which the lipoprotein pattern is to be electrophoretically determined, which method comprises adding non-reducing sugars to the plasma, plasma fractions or sera so as to obtain a mixture, lyophilizing said mixture so as to obtain a lyophilizate, and reconstituting said lyophilizate prior to determination.

2. A method as set forth in claim 1, wherein the non-reducing sugars are added in an amount of 10 to 20% w/v.

3. A method as set forth in claim 1, wherein sucrose is used as non-reducing sugar.

4. A method as set forth in claim 3, wherein sucrose is added in an amount of 10 to 20% w/v.

5. A method as set forth in claim 1, further comprising the steps of shock-freezing the sugar-containing mixture at at least −70° C. prior to lyophilization, subsequently heating said mixture to −40° C. to −35° C., and lyophilizing said mixture.

6. A method of using the sera preserved in accordance with the method set forth in claim 1, 2, 3, 4 or 5 as lipoprotein-electrophoresis control sera for plasma and serum examinations.

* * * * *